(12) United States Patent
Mills et al.

(10) Patent No.: US 7,729,784 B2
(45) Date of Patent: Jun. 1, 2010

(54) CONTACT ELECTRODE

(75) Inventors: Desmond Bryan Mills, Cheltenham (GB); Kevin Herbert, Cheltenham (GB)

(73) Assignee: The Dezac Group Limited, Cheltenham, Gloucestershire (GB)

( * ) Notice: Subject to any disclaimer, the term of this patent is extended or adjusted under 35 U.S.C. 154(b) by 396 days.

(21) Appl. No.: 10/488,884

(22) PCT Filed: Sep. 9, 2002

(86) PCT No.: PCT/GB02/04110

§ 371 (c)(1),
(2), (4) Date: Mar. 8, 2004

(87) PCT Pub. No.: WO03/022146

PCT Pub. Date: Mar. 20, 2003

(65) Prior Publication Data

US 2004/0199237 A1 Oct. 7, 2004

(30) Foreign Application Priority Data

Sep. 7, 2001 (GB) ................................ 0121660.5

(51) Int. Cl.
*A61N 1/00* (2006.01)
(52) U.S. Cl. ..................................................... 607/142
(58) Field of Classification Search .................. 607/142
See application file for complete search history.

(56) References Cited

U.S. PATENT DOCUMENTS

| | | | |
|---|---|---|---|
| 3,642,008 A | 2/1972 | Bolduc | |
| 4,173,221 A * | 11/1979 | McLaughlin et al. | 600/508 |
| 4,687,004 A | 8/1987 | Zenkich | |
| 4,798,208 A * | 1/1989 | Faasse, Jr. | 600/392 |
| 4,820,263 A * | 4/1989 | Spevak et al. | 604/20 |
| 4,834,103 A | 5/1989 | Heath | |
| 5,295,482 A * | 3/1994 | Clare et al. | 600/385 |
| 5,356,428 A * | 10/1994 | Way | 607/142 |
| 5,579,919 A | 12/1996 | Gilman et al. | |
| 5,617,853 A | 4/1997 | Morgan | |
| 5,875,892 A * | 3/1999 | Martin et al. | 206/459.1 |
| 5,984,102 A | 11/1999 | Tay | |
| 6,075,369 A | 6/2000 | Morgan | |
| 6,324,896 B1 * | 12/2001 | Aoyagi et al. | 73/29.01 |
| 6,418,332 B1 * | 7/2002 | Mastrototaro et al. | 600/316 |

(Continued)

FOREIGN PATENT DOCUMENTS

WO 97/43000 11/1997

*Primary Examiner*—George Manuel
(74) *Attorney, Agent, or Firm*—Young & Thompson

(57) ABSTRACT

An electrode generally comprises a body, which makes up the electrode and which is formed as a thin flexible polymeric substance such as urethane foam. The electrode body includes a central inner conductive area, which is associated with a first electrode connector. Around the inner conductive area is a non-conductive area formed as a ring around the inner conductive area and there is also an outer conductive area provided as a ring, concentrically arranged around the non-conductive area. Electrode connector (6B) is connected to the outer conductive ring. The electrode body, which has a release tag and is supported on a backing sheet and body can be peeled off the backing sheet using the release tag. The condition of the electrode can be evaluated using a test device, which can for example measure electrical impedance across the electrode via electrodes (6A) and (6B).

10 Claims, 2 Drawing Sheets

U.S. PATENT DOCUMENTS 6,603,318 B2 * 8/2003 Hansen et al. .............. 324/689
6,658,291 B2 * 12/2003 Snyder .......................... 607/8
2002/0137997 A1 * 9/2002 Mastrototaro et al. ....... 600/345

* cited by examiner

CONTACT ELECTRODE

The present invention relates to a contact electrode and in particular to a medical electrode of the type used with a defibrillator. In addition, the invention relates to a device for testing the condition of an electrode prior to use.

Known medical contact electrodes usually comprise a gel sheet, which includes an adhesive layer so that the electrodes can be attached to a patient's body. Electrodes are shown in U.S. Pat. No. 5,724,984 which discusses a multi-segmented electrode, U.S. Pat. No. 5,295,462, which deals with large surface electrodes and U.S. Pat. No. 4,257,424 which discusses electrodes that include a gel sponge in a non-conductive sheet forming the main body of the electrode.

Electrodes are prone to degrading with time due to drying of the gel and/or adhesive of the electrode. Electrodes that have a poor connection to a patient can result in poor monitoring and treatment. In the case of a defibrillator electrode, this could result in a misdiagnosis and improper treatment of a patient.

However, with such electrodes, there is no means to indicate whether an electrode is suitable to use before being connected to a device. Knowing the condition of an electrode is particularly important for Automated Electronic Defibrillators (AEDs), where a spare set of electrode pads for a defibrillator, could sit in storage for years before suddenly being required for use. If there is a clear indication of the condition of an electrode, then this would help to reduce wastage as, presently, electrodes include a "use by" date after which they are scrapped, even though they could be suitable for use.

According to a first aspect of the invention there is provided a contact electrode having a self-test facility, which can be used to indicate the conductive condition of the electrode.

Preferably, the electrode is a medical electrode.

It is preferred that the electrode includes at least one conductive area and a non-conductive area. Ideally, the electrode is substantially circular in a horizontal plane and incorporates two conductive areas comprising an inner area and an outer concentric, preferably circular, ring in said horizontal plane, separated by a non-conductive area.

It is envisaged that the electrode includes a power source, although power could be derived from the device into which the electrodes are plugged and an indicator or means to pass the indication to the device into which the electrodes are plugged. The indicator can then be used to show the condition of the electrode. Preferably, this is by measuring electrical impedance of the electrode.

A preferred indicator is an LED display although other indicators such as an audible alarm may be used. The LED display may be integral with the electrode. Alternatively, the electrode can be attached to an external display, for example a computer screen, which would give a visible output of the electrode's condition. In a preferred embodiment data such as the impedance of the electrode could be transferred directly to medical equipment such as an AED. This data could then be evaluated and used by the medical equipment to provide optimum treatment of a patient, taking into account the electrode condition.

Preferably, the indicator provides a direct indication of the condition of the electrode or alternatively, it may show the remaining life left for the electrode, based on predetermined parameters.

An alternative embodiment of this aspect of the invention involves providing an electrode where the self-test facility measures a physical, electrical or chemical parameter of the electrode. Preferably, the physical parameters that are measured are the temperature of the electrode or moisture content. Such measurements can provide an immediate warning that gel included in the electrode has dried and that the electrode or electrode pad will need replacing. It is envisaged that the self-test facility may combine electrical and physical self-testing.

Preferably, in another embodiment, the indicator of the condition of the electrode is a dye. Ideally, the dye is an environmentally friendly material such as an iron compound that changes colour according to levels of moisture in the electrode.

It is preferred that the dye is included in the electrode itself. Alternatively the indicator may be incorporated in the packaging for the electrode, preferably by way of a humidity-indicating card with characteristics similar to the gel of the electrode so that the electrodes can be easily monitored for condition.

It is also envisaged that a combined system, where both the electrode and the packaging includes an indicator to provide a double check of the electrode's condition.

It is preferred that self-testing is on a periodic basis, which can be activated manually or as part of an automated self-test routine governed by time, or in response to a specified event, such as changes in temperature or moisture levels. However, it is possible that the self-testing is on an aperiodic/random basis.

A consequence of effective defibrillation is the burning of tissue caused by the high electrical currents required. Regions of high-density current found in areas of poor contact or other charge collection points on the pad-skin interface cause this tissue burning. (Another phenomenon that causes tissue burning is edge effect, which occurs when there is high charge density).

According to a second aspect of the invention there is provided a substantially planar electrode having an inner area extending to an outer circumferential edge, said outer circumferential edge having a higher resistance than the inner area of the electrode.

Preferably, the outer circumferential edge is contoured in a horizontal and/or the lateral plane.

By having a contoured edge, rather than harsh outlined edges, for example in the case of a square electrode, then the risk for burning of the patient is reduced. This is because by having a minimal number of sharp edges/contours there is less attraction of charge, which causes the burning. A wider surface area would result in a lower charge distribution.

In a preferred embodiment, the resistance from the electrode centre to the circumferential edge is gradually increased, and preferably the optimum resistance gradient would rise to the resistance of the patient's skin. This helps to prevent a build up of charge by dispersing current more evenly and avoids sudden changes in resistance or "resistance-interfaces".

It is preferred that a lead to the electrode is connected to the centre of a pad making up the electrode so that charge is distributed evenly. It is envisaged that the lead is also connected to fine wire or strips of conductive material, which deposit the charge over the pad evenly.

Preferably the resistance of the electrode can be increased by reducing the amount of conductive material deposited towards the circumferential edge of the electrode, or by adding an insulate contaminant. In an alternative arrangement, the conductive material is layered in increasing thickness towards the centre of the electrode. The electrode of the second aspect of the invention may be of the form of that as discussed in the first aspect of the invention.

A further aspect of the invention provides a device for testing the condition of an electrode prior to use, said device including a power source, a sensor for measuring the electrical impedance of the electrode and indicator for displaying the condition of the electrode based on the impedance.

Preferably, the device is used on electrodes as previously described.

It is preferred that the device is connected to the end of leads attached to the electrodes and the device can then be attached to medical equipment, such as a defibrillator. Preferably, the device can transfer data about the electrodes to the medical equipment to assist the functioning thereof, based on the information about the electrode.

It is envisaged that the device can be in the form of a fixed attachment to an electrode lead or alternatively, it can be a plug on member that can be releasably attached to different electrode leads as required.

It is preferred that the device includes an indicator, preferably an LED to indicate the condition of the electrodes. Preferably the sensor compares the measured impedance with designated values for the electrode and indicates whether or not the impedance falls within these values. Other indicators could be used including an electronic display or audible alarm or otherwise indicator.

Also, the electrode may include circuitry to calculate impedance degradation measured in time, to give an indication as to the predicted time of electrode failure. This could be displayed as the number of useful days remaining.

The device may include a control activated by means of a user pressing a switch housed in the connector, or by means of a periodic or time interval. Furthermore, the test may be initiated by events such as a change in temperature or moisture level.

An embodiment of the invention will now be described by way of example, with reference to the accompanying drawings in which.

Figure 1:
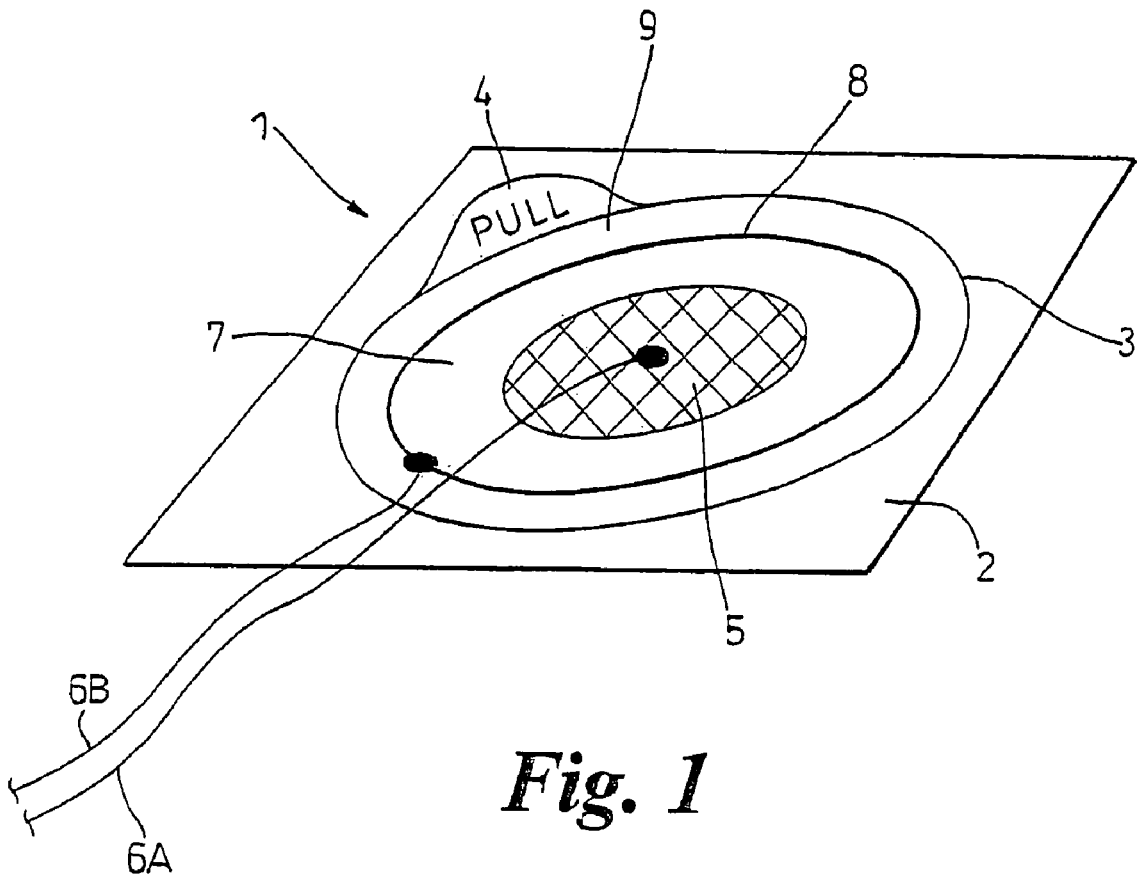
FIG. 1 shows an electrode forming a defibrillation pad.

As can be seen from FIG. 1, the electrode in its prior use state, is generally shown as 1. The electrode comprises a body 3 which forms electrode making up for example, a defibrillation pad. The body 3, comprises a number of components. These components, which are not shown in detail, comprise a non-conductive area forming a base layer. This is preferably constructed of a thin, flexible polymeric substance such as urethane foam, or a polyester, closed cell polyethylene or polyolefin laminate which provides structural and insulative properties. The main part of the base layer is furthest from the patient.

The next component is the conductive area, which preferably is a homogenous, solid, thinly deposited metallic substance, or a conductive ink material.

Alternatively the conductive area may be formed of a flexible mesh material, a conductive adhesive or a deposited ink pattern. Flexible conductive ink compounds known in the art have conductive fillers of gold, silicon, aluminium or other conductive materials.

The function of the conductive layer is to transfer (disperse) current or voltage from a lead on the electrode, to the lead in a sensing application, to the patient contact layer. Ideally, the base layer has a surface area that is slightly larger than the contact layer.

The electrode body includes a central inner conductive area 5 to which is attached a first electrode connector 6A. Around the area 5, is a non-conductive area 7 forming a ring around the conductive area 5. An outer conductive ring 8 is concentrically arranged around the non-conductive area and an electrode connector 6B is connected to the outer conductive ring. Concentrically arranged around the outer conductive ring is the edge area 9 of the electrode, which has a circular contour.

The electrode connectors 6A, 6B are preferably insulated wire conductors that extends from attachment points with the conductive layer. Alternatively, the electrode connectors can be insulated wire conductors and conductive strips, or traces deposited between the contact layer and the base or conductive layers. Such a trace or strip may also extend just, beyond the base layer for connection with an ancillary connection means such as a wiring harness including a conductive clip.

The electrode is attached to a patient by a patient contact layer which is preferably a thin layer of semi-liquid gel material. The gel maintains direct electrical contact with the skin to reduce variations in conductance. The gel ideally is a conductive gelatinous compound, which is also flexible for controlled adhesion to the body of a patient. The gel also preferably has a pressure sensitive, moisture resistant adhesive property as found in polymer hydrogels.

The patient contact layer is preferably smaller than the body of the electrode. Consequently, an outer edge of electrode will come into contact with the patient and thus may have a pressure sensitive adhesive disposed on its patient contact side for increased adhesion to the patient.

Typically, when the electrode is not in use, it is releasably attached to a sheet 2 forming a backing layer. The backing layer comprises of a conductive sheet or a non-conductive sheet having a conductive area in order to complete a circuit between the outer and inner conductive areas of the electrode. The electrode can be removed from the sheet by pulling on release tag 4.

The electrode or its packaging may include an indicator to give a visual indication of the condition of the electrode. Until recently the only indicating gel used a small concentration (between 0.5 and 1.0% weight for weight) of moisture sensitive cobalt chloride indicator, which gives a blue gel. This changes to pink as it absorbs moisture and becomes saturated, returning to blue as it is regenerated.

However, due to the highly toxic effects of cobalt chloride, manufacturers have been moving towards more environmentally friendly indicators allowing for a wider use than previously possible. One such indicator uses an iron compound that changes from orange to colourless as it absorbs water.

When stored, pairs of electrodes may have a separating layer between them (not shown). The separating layer may include a strip of moisture sensitive/indicating material.

Alternatively, the entire separating layer is made of moisture sensitive/indicating material. Also, it may be that the backing layer of each electrode contains a strip of (or is covered entirely with) moisture indicating material. The backing layer may be mixed with the moisture sensitive compound or alternatively, or in addition to this, the adhesive gel is mixed with the moisture sensitive compound.

Potential users can then see the condition of the pads via the card, strip, moisture indicating material/compound through a window or other means of showing the condition outside of the packaging. Thus it is possible to immediately see the condition of the electrodes by the colouring.

Furthermore, the indicator substance could be applied to the area to show a warning symbol when electrode failure occurs.

Figure 2:
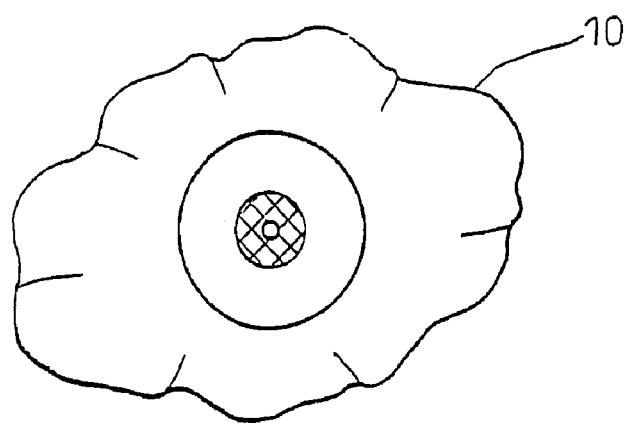
FIG. 2 shows a variation of an electrode shown in FIG. 2, having a wave outer edge.

Although a circular edge area is shown in FIG. 1, it is possible for the outer edge of the electrode to have alternative shapes. For example, as shown in FIG. 2, a wave arrangement may be used so providing the electrode with a shape having gently curving contoured edge 20. The resistance of the electrode is also matched to that of the patient's skin. This prevents a build up of charge by dispersing the current evenly and results in a lower current density at a set applied voltage. Ideally, the optimum resistance gradient would rise from electrode resistance to skin resistance in the shortest possible distance/space without causing resistance-interfaces. However, this invention is not limited in any way to this value.

In a further embodiment, the pad circumference is increased to distribute the outer edge charge over a wider length, thus reducing the charge density. Preferably, the shape of the pad edge also is waved in that it has a crinkled or irregular edge. This has the effect of again increasing the circumference for a given area.

Figure 3:
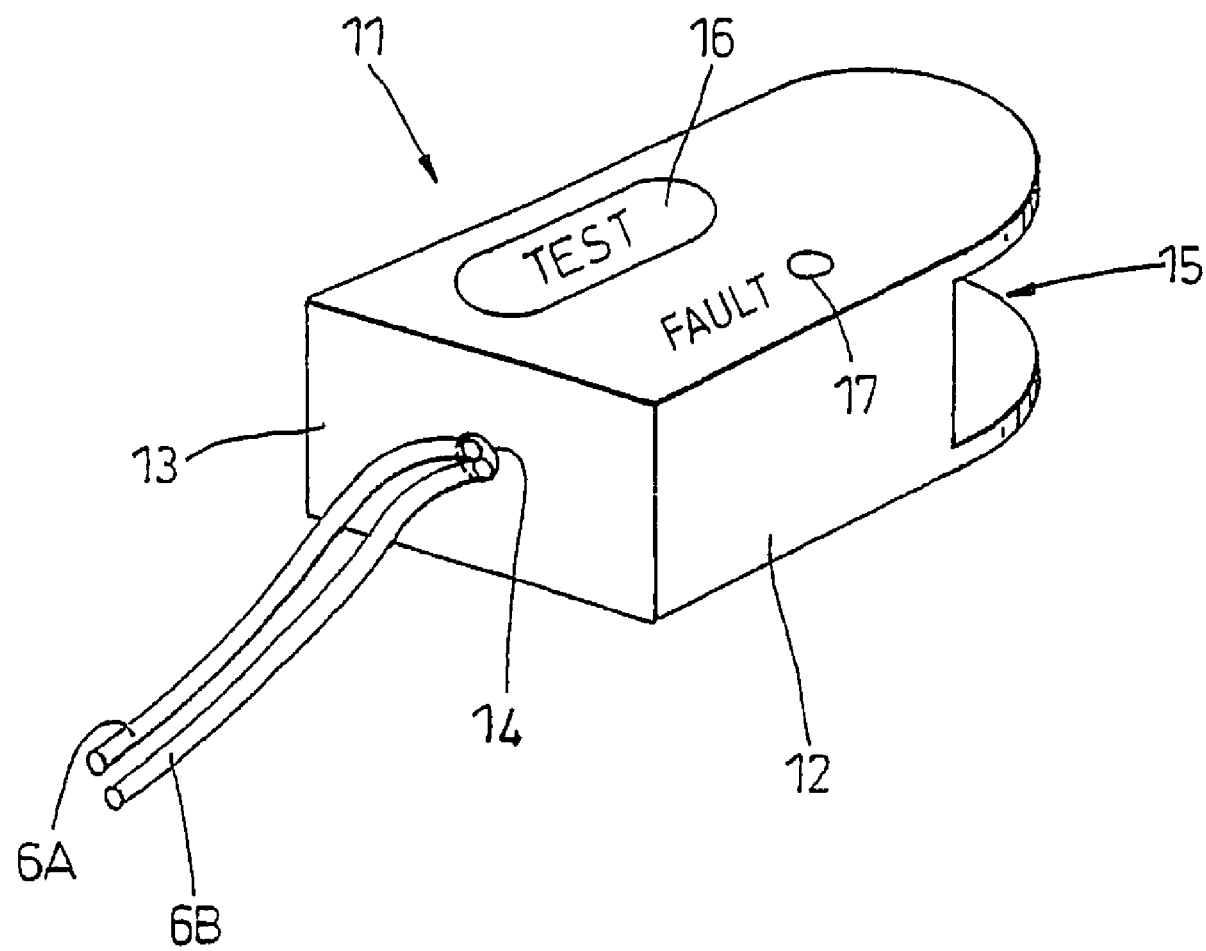
FIG. 3 shows a test device for measuring the status of an electrode.

A device for testing the electrode shown in FIGS. 1 and 2, is shown in FIG. 3. The device, which is generally shown as 11, comprises a body 12 a first end of which 13 has a connector 14 so that the device can be fitted to electrodes 6A, 6B. At the opposing end of the body, there is a connecting part, which allows the device to be attached to a piece of medical equipment, such as a defibrillator. Preferably, the connector 15 allows for automatic activation of the test device when it is attached to the medical equipment. This may be by having a connector that on attachment is pushed into position to complete circuitry, so switching power to the device 11. On activation of a switch 16 on the device body 12, power is transmitted to the electrodes and if this is not within parameters set by the device, then a fault is indicated by fault button 17. The fault may be indicated by a simple visual indication such as the flashing of a warning light or more significant information may be provided about the electrode status by for example, an LED display.

When the electrodes are to be self tested the control circuitry connects the battery to the electrode circuit through a switch. Current of a known value flows from the battery, up the electrode leads to the first conductive area of the electrode, across the conductive sheet and then through the second conductive area back via the second electrode lead back to the battery. It is envisaged that the electrodes could have one single area of conduction and form a circuit through the conductive sheet separating them.

The monitoring circuitry measures electrical parameters associated with the electrodes. For a known voltage the electrode impedance can be calculated and provide an indication of the pad's effectiveness prior to and during use.

Although preferred illustrative embodiments of the present invention are shown above, it will be evident to one skilled in the art, that various changes and modifications can be made, without departing from the spirit and scope of the invention.

The invention claimed is:

1. An electrode assembly for connection in use to a separate electrical device, said electrode assembly comprising two spaced conductive layers for making electrical contact with a patient in use, a backing sheet overlying both said contact electrode layers, said backing sheet electrically conductively interconnecting said contact electrode layers and forming the sole electrically conductive connection between said contact electrode layers, said backing sheet being readily peelable from said conductive layers, a test circuit for passing a current through a circuit including both contact electrode layers and an electrically conductive portion of said backing sheet to test the conductive condition of the contact electrode layers, and connection means for connecting said assembly to said test circuit, said test circuit including means for electrically testing and indicating the condition of said contact electrode layers.

2. An electrode assembly as claimed in claim 1, wherein said test circuit is integral with said connection means to form a plug so that the electrode assembly can be plugged into said test circuit to allow the transmission of test data from the test circuit to an electrical device via said connection means.

3. The electrode assembly according to claim 1, wherein one said contact electrode layer forms an inner area and the other said contact electrode layer forms an outer area surrounding said inner area, said areas being separated by a non-conductive area of the electrode assembly.

4. The electrode assembly according to claim 3, wherein the inner layer is circular and is substantially in the center of the electrode, the non-conductive area forming a ring around said inner layer and the outer layer forming a concentric border around said non-conductive area.

5. The electrode assembly according to claim 3, wherein an outer circumferential edge of the outer area has a higher resistance than said inner area of the electrode.

6. The electrode assembly according to claim 5, wherein the resistance from the electrode assembly center to said outer circumferential edge increases gradually.

7. The electrode assembly according to claim 1, wherein an extension of one said conductive layer is provided to form a release tag so that the conductive layers may be pulled from said sheet by pulling on said release tag.

8. The electrode assembly according to claim 1, wherein said connection means comprises wires individually attached each to a respective one of said contact electrode layers.

9. The electrode assembly according to claim 1, which is adapted to test the conductive condition of the contact electrode layers prior to application to the patient.

10. An electrode assembly for connection in use to a separate electrical device, said electrode assembly comprising two spaced conductive layers for making electrical contact with a patient in use, a backing sheet overlying both said contact electrode layers, said backing sheet electrically conductively interconnecting said contact electrode layers and forming the sole electrically conductive connection between said contact electrode layers, and said backing sheet being readily peelable from said conductive layers, and connection means for connecting said assembly to a test circuit for electrically testing and indicating the condition of said contact electrode layers.

* * * * *